United States Patent [19]

Sealfon et al.

[11] Patent Number: 4,781,689
[45] Date of Patent: * Nov. 1, 1988

[54] SPRING-OPERATED LIQUID-DISPENSING DEVICE

[76] Inventors: Andrew Sealfon, 713 North St., Middletown, N.Y. 10940; Carl Yurdin, 2 Harbor View Rd., Port Washington, N.Y. 11050

[*] Notice: The portion of the term of this patent subsequent to May 8, 2001 has been disclaimed.

[21] Appl. No.: 930,657

[22] Filed: Nov. 13, 1986

[51] Int. Cl.⁴ .............................................. A61M 7/00
[52] U.S. Cl. .................................... 604/134; 604/214; 222/95
[58] Field of Search ................................ 604/134–141, 604/214; 222/95, 103, 94, 92, 103, 105; 128/DIG. 12

[56] References Cited

U.S. PATENT DOCUMENTS

| | | | |
|---|---|---|---|
| 3,565,292 | 2/1971 | Jinotti | 222/103 |
| 3,677,246 | 7/1972 | Stein | 604/136 |
| 4,265,241 | 5/1981 | Portner et al. | 604/134 |
| 4,447,232 | 5/1984 | Sealfon et al. | 604/134 |
| 4,539,005 | 9/1985 | Greenblatt | 604/141 |
| 4,557,728 | 10/1985 | Sealfon et al. | 604/134 |
| 4,578,060 | 3/1986 | Huck et al. | 604/134 |

Primary Examiner—Barry S. Richman
Assistant Examiner—Wallen T. J.
Attorney, Agent, or Firm—Myron Amer

[57] ABSTRACT

A housing having exterior lateral side walls, top and bottom side walls and a single internal wall running adjacent to a lateral side wall. The housing defines an internal rectangular compartment and a parallel side track between the adjacent internal and external walls. A collapsible bag filled with liquid and a slide member, actuable by a constant torque spiral spring are located in the compartment. The slide member has a boss fitting and cooperating with the track to allow the slide member to freely slide without a rotative component under action of the spring.

2 Claims, 2 Drawing Sheets

SPRING-OPERATED LIQUID-DISPENSING DEVICE

BACKGROUND OF THE INVENTION

The present invention relates to a portable liquid dispensing device for subcutaneous, intravenous and similar feeding of liquids such as medicaments and the like.

We have previously disclosed in our U.S. Pat. No. 4,447,232, issued on May 8, 1984 (commonly assigned to the assignee hereof) a portable liquid dispenser particularly adapted for the constant rate feeding of medication and the like to fully ambulatory patients. The apparatus disclosed in the aforesaid patent has had wide commercial success and is in use throughout the world.

In this patent, a collapsible bag is located along with a piston-like slide member in a housing. A constant force spring acts on the slide member to exert a constant pressure on the bag. The front cover of the housing is provided with a slot, while the slide member is provided with a rectangular lug passing through the slot. The slot and lug provide tracking and alignment to the slide member since the lug which fits (with tight tolerances) into the slot prevents rotation of the slide member. A clip, which is a part of a fitting on the case, permits the lug to be locked and thereby removes pressure from the fluid reservoir.

This worked quite well, although somewhat complexly to produce. Also, the external clip extended beyond the surface of the housing which increased the overall thickness of the device. In addition, when worn on the body, the lug and clip tended to snag on clothing or undergarments and could not be concealed in a trouser pocket. The slot, furthermore, constituting an opening through which the liquid bag was visible represented an external channel through which contamination and damage to the bag could occur. Thus, the need to simplify the construction of such a device is apparent to render it more easy to use, to lower the cost thereof, and to provide greater reliability and greater accuracy in dose dispensing.

It is, therefore, the object of the present invention to provide an improved liquid dispensing device for subcutaneous, intravenous, and/or similar medicament feeding characterized by its simplicity of construction, ease of operation and great reliability.

The foregoing objects, together with numerous other objects and advantages will be apparent from the following disclosure.

SUMMARY OF THE INVENTION

According to the present invention the device for dispensing liquids according to the present invention is formed of a flat parallelepiped housing having a pair of opposed members cooperating to form lateral side walls, and transverse top and bottom end walls defining a rectangular shaped internal compartment adapted to receive a supply of liquid in a collapsible bag resting against the bottom transverse end wall and a rectangular slide member movable from the top transverse end wall in contact against the bag. An internal wall is provided, within the housing, parallel to and spaced a short distance from one of the external side walls. The internal wall and its adjacent external side wall are each provided with substantially coextensive elongated slots and cooperate to form a track extending parallel to the length of the internal rectangular compartment. A boss member integrally formed with the slide member, extends from a lateral edge of the slide member into the track and cooperates with the track to prevent canting of the slide member within the internal compartment as it presses against the bag. A coil spring has one end affixed to the housing and its other end on a spindle rotatably mounted on the slide member, so that the coil spring winds about the spindle and at the same time urges the slide member with a constant torque against the bag.

The boss, extending from the slide member, is provided with a resilient latch which normally slides within the track between the internal wall and its parallel adjacent exterior wall, the exterior wall being provided with a detent located between the end of its slot and the top transverse end wall which detent is adapted to removably receive the resilient latch and hold the slide member out of pressure contact with the bag. The latch is releasable by pressing the same out of the detent, thereby allowing the coil spring to activate the slide member and press it against the bag to cause the liquid to flow outwardly. The boss is also provided with a finger grip which extends through the slots which permits the slide to be moved manually.

Preferably, the one end of the coil spring which is fixed to the housing is provided with a button, adapted to sit within a groove in the internal wall. The housing cover, when removed, allows the button to be removed from the groove, thereby permitting the entire spring as well as the other components to be disassembled. Also, the slide member is provided with a pair of spaced skirts extending below the bottom transverse end wall, toward the collapsible bag, which skirts at least a part surround and hold the collapsible bag, whereby the bag and the slide remain in constant engagement with each other.

Full details of the present invention are set forth in the following description and are illustrated in the accompanying drawings.

DESCRIPTION OF THE INVENTION

Figure 1:
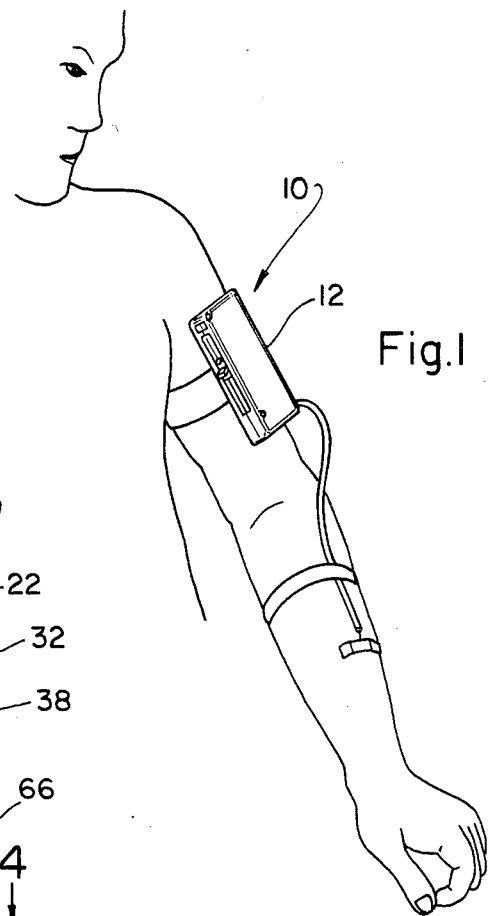
FIG. 1 is a perspective view of the liquid dispensing device embodying the present invention.
Figure 3:
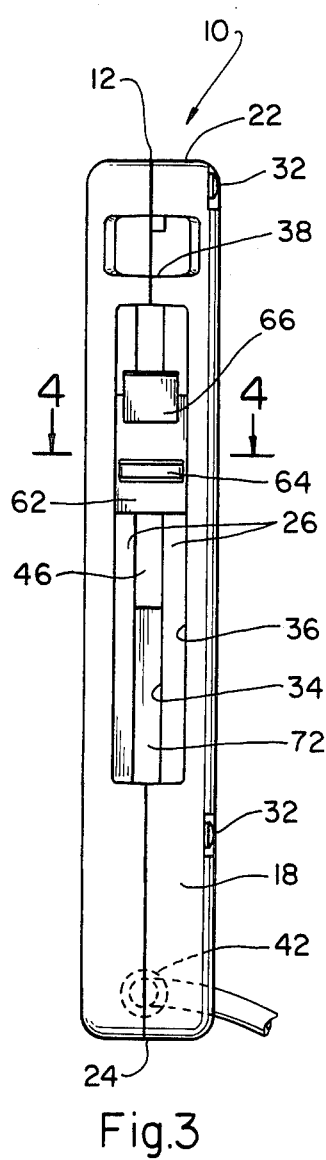
FIG. 3 is a side elevational view as seen in the direction of 3—3 in FIG. 2.
Figure 4:
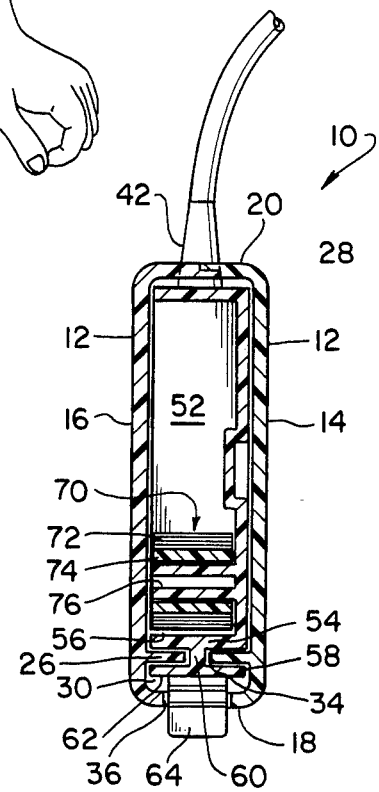
FIG. 4 is a sectional view along line 4—4 of FIG. 3.
Figure 2:
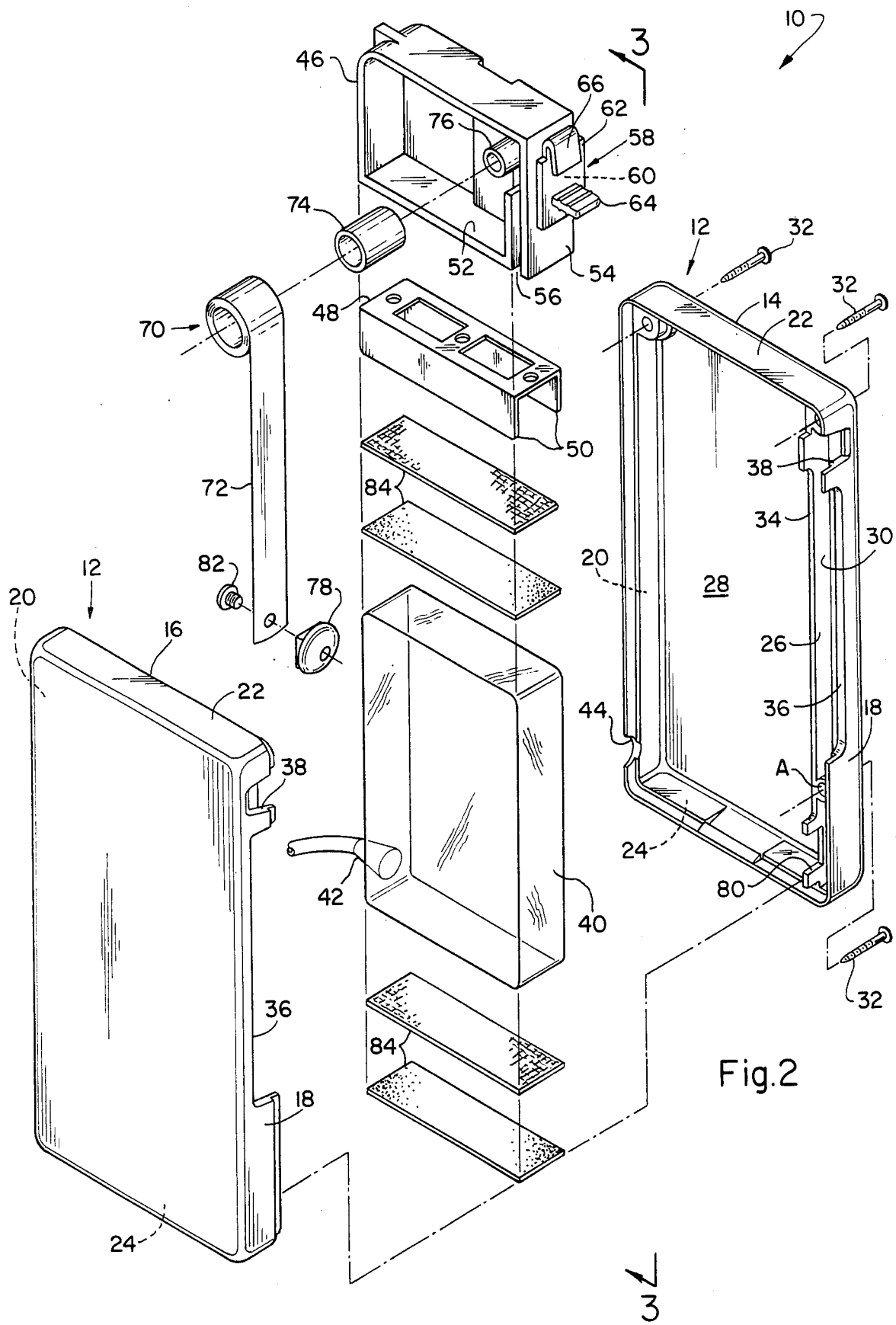
FIG. 2 is a perspective exploded view of the device shown in FIG. 1.

As seen in the drawings, the liquid dispensing device, generally depicted by the numeral 10 is formed of a housing 12 having a basic body member 14 and a cover 16 each having perpendicular peripheral edges shaped so that when assembled together they define parallel exterior side walls 18 and 20 and transverse top and bottom end walls 22 and 24, respectively. Extending parallel to one of the exterior side walls 18, and spaced a short distance therefrom is an internal wall 26. The housing thus bounds within it an internal rectangular compartment 28 and a narrow track 30 extending along its length. The housing body 14 and its cover 16 are joined together by a plurality of screws 32. Located in the internal wall 26 and its adjacent exterior wall 18, are elongated slots 34 and 36, respectively, which terminate in stop ends spaced from the respective top and bottom end walls 14 and 16. In the space between the top transverse end wall 14 and the end of the slot 36 is a rectangular detent opening 38.

It will be appreciated that for ease of manufacture, the housing is made in two parts. Functionally, however, since the body and cover combine to form an integral singular member their peripheral side edges are viewed combined into side walls, rather than separately as edge parts of either the cover or the body. Of course, it will be apparent that the body can be developed and constructed in a different manner.

The rectangular compartment 28 within the body 10 is such that there can be located adjacent the bottom transverse end wall 16 a collapsible bag 40 in which a supply of medicating liquid is contained. The bag 40 has an integral outlet/inlet valve member 42 capable of extending through a hole 44 in the exterior side wall 20 of the housing. The collapsible bag 40 is preferably made of strong flexible plastic material inert to medication, and is transparent so that the supply of liquid can be seen therethrough.

Also located in the compartment 28 is a rectangular box-like open-faced slide member 46 which has a transverse dimension slightly smaller than the transverse dimension of the compartment 28 so as to permit it to freely slide within the compartment 28. The slide member 46 is located between the top transverse end wall 14 and the bag 40 and is preferably, although not necessarily, provided with a holding member 48, formed in a pair of front and back depending skirts 50 adapted to engage about the upper end of the bag 40 so as to insure a positive engagement and contact with the bag, although allowing for the bag to be freely removed and replaced.

The lower wall 52 of the slide member is separated at one end from the adjacent lateral wall 54 of the slide member 46 so that a slight clearance 56 is provided communicating with the open interior portion of the slide member. Mounted on the lateral wall 54 of the slide member 46 is a boss 58 comprising a perpendicularly extending post 60 on which is centrally mounted in T-shaped fashion a rectangular tab 62. The post 60 is sufficiently large to pass through the slot 34 in the internal wall while the tab 62 seats within the track 30 between the interior and exterior side walls 26 and 18, respectively. The tab 62 thus rides within the track 30 while the lateral wall 54 of the slide member rides against the internal wall 26. The tab 62 is of such a thickness that while it slides freely in the track 30 its cooperation with the the internal and external walls 26 and 18 is such that it prevents the slide member 46 from canting or rotating within the compartment 28.

Extending perpendicularly outward from the tab 62 is a finger grip 64 which passes through the slot 34 in the exterior side wall 18, so that it can be grasped by the user from the exterior of the housing. Although it is not critical, it is preferred that the grip 64 be small so as not to extend too much beyond the side wall 18. Also mounted on the tab 62 is a U-shaped latch 66 which is shaped to have a sufficient resiliency so that it can ride within the space of the track 30 and upon reaching the detent opening 38 spring into the detent to be held therein, thereby maintaining the slide member 46 against movement. The latch 66 is depressible against its resilient bias, removing it from engagement within the detent 38 to allow the slide member to move, when desired.

To power the slide member 42 in sliding movement from an initial starting position, defined generally as the position adjacent the top transverse end wall 14, into urging and pressing position against the bag 40, so that the liquid within the bag can be forced out of the outlet 42, use is made of a constant torque spring generally designated by the numeral 70, of the type disclosed in our aforementioned patent. The constant torque spring 70 comprises an elongated metal band 72, affixed at one end to a spindle core 74 mounted about a fixed post 76 integrally formed with the slide member 46 so that the spindle is rotatable about the post 76. The metal band 72 is wound into a permanent spiral coil so that it is under constant tension or torque and its free end passes through the space 56 formed in the slide member 46 and is drawn downwardly parallel to the internal wall 26 and is held at the lower end of the housing. A button 78 is secured at the free end of the band 72 and fits within a hole 80 formed in the internal wall 26. When the two parts of the housing 12 are separated, the button 78 may be easily removed from the hole.

The torque spring 70 is a constant spring urgency to assume the form of the coil about the rotatable core 74. Under this urgency, the coil continuously tends to shorten the extended length of the metal band 72. Since the free end is fixed to the housing this bias urges the slide member 46 to move longitudinally in the compartment 28 from the top transverse end wall 14 toward the bottom transverse end wall 16, thus acting to compress the bag 40 as the liquid therein is consequently forced out of its outlet port 42. The force exerted by the spring 70 on the slide member 46 is constant and uniform so that the flow of liquid out of the bag 40 is correspondingly constant and uniform over a given time period. When it is, of course, desired to arrest or stop the flow of fluid from the bag 40, the slide member 46 is retracted, by acting on the finger grip 64 to lift the slide member 46 so that the latch 66 engages within the detent 38.

In a rather simple and inexpensive manner the present invention overcomes the normal tendency of a helical coil torque spring 70 to urge the slide member 46 to cant or have a rotative component of movement about the axis of the core 74. This tendency is neutralized simply by the cooperation of the boss 58 and, particularly, its tab 62 in cooperation with the internal and external slotted walls 26 and 18, respectively, as well as by the side wall 54 of the slide member 46 cooperatively sliding along the inner surface of the internal wall member 26, all parallel to and aligned with the slide member itself. Since it is preferred that the material from which the slide member 46 is plastic, the slide member 46, the boss 58, the latch mechanism 66, and the finger grip 64 can be all entirely molded, in situ, in an integral unitary form of very low frictional material. Thus, the separate finger grip, clip mechanism, and the screw mechanism as shown in our earlier patent can be avoided without any loss of function.

Furthermore, the slide member 46 may be more accurately dimensioned with respect to the inner dimensions of the compartment 28 so that smooth sliding movement can be obtained.

It will be seen from the drawings that the slots 34 and 36 formed in the internal and external side walls 26 and 18 respectively provide stop members for the boss 58 at each of their ends. It is, desired, however, to provide a more positive stop member at the lower end of movement of the slide member 46, and, therefore, one of screws 30 is located at the position A at the end of the effective traverse of the track 30 so that it can engage the boss 58 in its lower-most postion. It is also preferable to provide either the collapsible bag 40, or the slide member 46, or the bottom transverse end wall 18, or all of them with suitable Velcro pads, enabling insertion of the bag member properly, so as to eliminate any tendency for the bag to slide out of the desired position during operation.

While the present invention describes a number of differences in construction from that shown in our earlier patent, it will be appreciated that the operation of the device wherein the slide member compresses the collapsible bag so as to extrude the liquid therefrom, and wherein the bag has the ability to be refilled from the exterior through outlet/inlet 42, are all essentially the same as described in the aforementioned patent. Accordingly, should the reader require any additional information, reference is made to U.S. Pat. No. 4,447,232 as if more fully set forth herein.

It will be apparent from the foregoing that various beneficial effects are obtained from the present structure. Namely, by moving the tracking mechanism from the front cover to the side, the rotational tendency is greatly neutralized without complex structure and without effect on the free movement of the slide member. A much more compact device and superior tracking as required for accurate pressure gradients is obtained.

A significant advantage occurs from the placement of the spring over the guide track in that the spring also acts as a barrier against infiltration of dirt and the like thorugh the track on to the bag and prevents external contact with the bag. This also allows the tracking and movement of the slide member without impinging on clothing, irrespective of where it might be placed on the body. The latch residing in a detent opening on the side provides the same locking function as the clip shown in the earlier patent, while being sufficiently contained within the housing thereby the latch is allowed to move unimpeded by any external hindrance. Extensive tests have confirmed that steady flow and pressure (about 5% accuracy) occurs with no variations caused by binding of the slide member whatsoever.

Various modifications and changes have been alluded to herein and others will be apparent to those skilled in this art. Accordingly, it is intended that the present disclosure be taken as illustrative only and not as limiting of the scope of the invention.

What is claimed is:

1. A spring operated device for dispensing a liquid at a controlled rate comprising a rectangular housing formed of a pair of parallel and opposed side walls and two parallel and opposed end walls forming a rectangular shaped internal compartment therebetween, one of said side walls having a longitudinal slot opening into said compartment, an internal wall in said compartment spaced inwardly of and substantially parallel to said one of said side walls forming therebetween a guide track that is essentially parallel to said one of said side walls, said track having an upper end adjacent one of said end walls and a lower end adjacent the other one of said end walls, a collapsible bag disposed in said compartment, said bag adapted to store and dispense a liquid, a slide member disposed in said compartment, a constant torque, coiled spring disposed in said compartment, one end of said spring connected to said slide member, the other end of the spring connected to said housing so as to urge said slide member into pushing contact with said bag, said slide member adapted to move in said compartment between said end walls and thereby place a controlled pressure on said bag, and a boss rigidly connected to said slide member and extending from one side thereof through said longitudinal slot of said one of said side walls, said boss adapted to slide in and be constrained by said track so that as said slide member moves between said end walls, said slide member is caused to traverse a path at a maintained orientation relative to said side walls.

2. A spring-operated liquid-dispensing device as claimed in claim 1, including a finger grip attached to said boss and extending through the longitudinal slot of said one longitudinal wall, a detent aperture located on said one of said side walls proximate said upper end of said track, and a resilient U-shaped latch carried on said boss and adapted releasably to seat in said detent aperture whereby when manual displacement of said finger grip causes said boss to move into a position adjacent said detent aperture, said latch will snap into the same to hold said slide member out of pressured engagement with said bag.

* * * * *